United States Patent [19]

Priddy et al.

[11] Patent Number: 5,347,055
[45] Date of Patent: Sep. 13, 1994

[54] OLIGOMERS OF STYRENE AS FLEGMATIZERS FOR ORGANIC PEROXIDES

[75] Inventors: Duane B. Priddy, Midland, Mich.; Mehmet Demirörs, Terneuzen, Netherlands

[73] Assignee: The Dow Chemical Company, Midland, Mich.

[21] Appl. No.: 82,325

[22] Filed: Jun. 24, 1993

Related U.S. Application Data

[63] Continuation-in-part of Ser. No. 896,265, Jun. 10, 1992, abandoned.

[51] Int. Cl.$^5$ ............... C07C 409/00; B01J 31/02
[52] U.S. Cl. ............... 568/559; 502/160; 252/186.26; 252/186.42; 585/510; 585/520
[58] Field of Search ........... 585/502, 520, 570; 512/160; 526/89, 346, 347; 252/186.26, 186.42; 568/555

[56] References Cited

U.S. PATENT DOCUMENTS

| | | | |
|---|---|---|---|
| 2,620,330 | 12/1952 | Park | 260/93.5 |
| 3,129,206 | 4/1964 | Pajaczkowski | 260/88.7 |
| 3,290,257 | 12/1966 | Bader et al. | 502/160 |
| 3,507,808 | 4/1970 | Douglas et al. | |
| 3,650,972 | 3/1972 | Sanchez | |
| 3,810,920 | 5/1974 | Bafford et al. | |
| 3,907,903 | 9/1975 | Chang et al. | |
| 3,917,745 | 11/1975 | D'Angelo et al. | |
| 3,947,418 | 3/1976 | Priddy | |
| 3,948,891 | 4/1976 | Priddy | |
| 3,948,907 | 4/1976 | Priddy | |
| 4,029,685 | 6/1977 | Priddy | |
| 4,072,810 | 2/1978 | D'Angelo et al. | |
| 4,079,074 | 3/1978 | Sanchez et al. | |
| 4,178,263 | 12/1979 | Priddy | |
| 4,219,676 | 8/1980 | Sanchez et al. | |
| 4,396,526 | 8/1983 | Woodson et al. | 252/186.22 |
| 4,455,252 | 6/1984 | Wylegala et al. | 252/186.26 |
| 4,469,862 | 9/1984 | Komai et al. | |
| 5,043,404 | 8/1991 | Mahabadi et al. | 526/194 |

FOREIGN PATENT DOCUMENTS 2829807 1/1979 Fed. Rep. of Germany .
915009 1/1963 United Kingdom .

OTHER PUBLICATIONS

Chemical Abstract 92:42628r (1992).
Derwent 83-836821/49 (1983).
Derwent 87-167596/24 (1987).
Chemical Abstract 106:19159n (1987).
Derwent 30369Y-17 (1990).
Derwent 84-060915/10 (1984).
Derwent 83-781713/40 (1983).
Derwent 01971C/02 (1978).
Derwent 87118P (1966).

Primary Examiner—Asok Pal
Assistant Examiner—P. Achutamurthy

[57] ABSTRACT

A flegmatizer, which is an oligomer of styrene or of styrene and at least one comonomer, is admixed with an organic peroxide to reduce the heat- and/or shock-sensitivity of the peroxide. The resulting composition can be employed to polymerize olefinic monomers.

20 Claims, No Drawings

OLIGOMERS OF STYRENE AS FLEGMATIZERS FOR ORGANIC PEROXIDES

CROSS-REFERENCE TO RELATED APPLICATION

This is a continuation-in-part of application Ser. No. 07/896,265, filed Jun. 10, 1992, now abandoned.

BACKGROUND OF THE INVENTION

The present invention relates to the use of shock- and/or heat-sensitive organic peroxides as initiators for the polymerization of olefinic compounds.

Many organic peroxides are known and used to initiate polymerization of monomers containing olefinic unsaturation. Many such peroxides are shock sensitive and usually are handled only in diluted form. Generally, the addition of an appropriate diluent reduces the shock sensitive of the organic peroxide to the point where it can be safely handled. The problem of shock sensitivity of such peroxides has been recognize for many years. See, e.g. U.S. Pat. No. 4,178,263, which discloses diluting the peroxide with an olefinically unsaturated monomer which does not homopolymerize. According to said patent, monomers which exhibit no tendency to homopolymerize are those monomers which in admixture with an organic polymerization-inducing peroxide do not polymerize to more than one percent conversion of monomer to polymer at 100 hours at 40° C. when the organic peroxide and monomer are present in a one-to-one ratio by weight. Typical non-homopolymerizing monomers include: maleic anhydride, dimethyl maleate, diethyl maleate, citriconic anhydride, dimethyl citriconate, methyl citriconate, ethyl citriconate, fumaronitrile, methyl fumuarate, dimethyl fumuarate, ethyl fumurate, diethyl fumuarate, cinnamonitrile, methyl cinnamate, ethyl cinnamate, stilbene, and the like. These monomers readily copolymerize with the basic monomer present, e.g. styrene.

When diluted peroxide compositions are employed in the free-radical polymerization of olefinically unsaturated materials, the diluent material frequently has a deleterious effect on the resulting polymer; for example, in the polymerization of polystyrenes the presence of oils, hydrocarbon diluents, high molecular weight hydrocarbons and the like are not readily removed from the polymer after polymerization and result in a reduction in the heat-distortion temperature. When polymers made with organic peroxides are used in food contact applications, the diluent used with the peroxide must be nontoxic. In many countries, approval by a government agency is required for use of the diluent in the polymer. In the case of styrenic polymers, the list of additives which meet the requirements for a good flegmatizer and which are also approved for food contact applications is very small. Examples of known flegmatizers include dioctyl phthalate, fatty acid esters, epoxidized soybean oil and mineral oil. Of these, only mineral oil and epoxidized soybean oil are approved over a wide geographic area for use in food contact applications. While mineral oil is approved for use in the preparation of polystyrene for food contact applications, it is not a good flegmatizer for some new, highly polar initiators, as they are not soluble in the relatively nonpolar mineral oil.

In view of the deficiencies of the prior art solutions to the problem of flegmatizing organic peroxides for use in the polymerization of olefinically unsaturated monomers, it would be desirable to have a flegmatizer which is suitable for food contact applications, and which has polarity sufficient to be compatible with highly polar initiators. Additionally, it would be desirable to have a flegmatizer which is an inert material, and which can easily be mixed with organic peroxide initiators to make them safe and easily handled.

SUMMARY OF THE INVENTION

The present invention includes such a flegmatizer, which is an oligomer of styrene or of styrene and at least one comonomer. Accordingly, the present invention includes a storage stable organic peroxide composition having reduced heat-and/or shock-sensitivity, the composition comprising an organic peroxide and from about 10 to about 90 percent, based on the total weight of the flegmatizer and the peroxide, of a flegmatizer comprising an oligomer of styrene, or of styrene and at least one comonomer.

In a second aspect, the invention is a method for reducing the heat- and/or shock-sensitivity of an organic peroxide, the method comprising admixing an organic peroxide with from about 10 to about 90 percent, based on the total weight of the flegmatizer and the peroxide, of a flegmatizer comprising an oligomer of styrene, or of styrene and at least one comonomer.

In another aspect, the invention is a method for polymerizing one or more olefinically unsaturated monomers, the method comprising admixing an organic peroxide with from about 10 to about 90 percent, based on the total weight of the flegmatizer and the peroxide, of a flegmatizer, and using the resulting mixture for the polymerization of an olefinically unsaturated polymerizable material, the flegmatizer comprising an oligomer of styrene or of styrene and at least one comonomer.

Advantageously, the flegmatizers of the present invention are compatible with a wide variety of organic peroxide initiators, are highly compatible with styrene-containing polymers and provide mixtures of organic peroxides which are safely and conveniently handled, and are suitable for use in food contact applications for styrenic polymers.

Polymers made using the flegmatizers of the present invention are useful in food packaging applications including, for example, packaging for yogurt, cookies, dairy products, fresh produce and meat.

DETAILED DESCRIPTION OF THE INVENTION

In the present invention a flegmatizer is employed with an organic peroxide in the polymerization of an olefinically unsaturated monomer.

The organic peroxides which can be employed in the present invention include shock- and/or heat-sensitive organic peroxides including, for example, propionyl peroxide, acetyl peroxide, succinic acid peroxide, t-butyl peroxyisobutylate, cyclohexanone peroxide, methyl ethyl ketone peroxide, 2,2-bis-(t-butyl peroxy)-butane, 1,1-bis(t-butyl peroxy)cyclohexane, di-(t-butylperoxy)azelate, t-butyl peroxy isopropyl carbonate, 2,5-dimethyl-2,5-bis(benzoylperoxy)hexane, t-butylperacetate, t-butylperbenzoate, and di-t-butylperoxy phthalate peroxide, benzoyl peroxide and 1,1-bis-t-butylperoxy-3,3,5-trimethylcyclohexane. Preferred organic peroxides are perketals, peresters and percarbonates. Mixtures of organic peroxides can be employed.

By the term "reduced shock-sensitivity" is meant a reduced $E_{50}$ value as determined by Liquid Propellant Information Agency Test No. 4, Drop-Weight Test, Joint Army-Navy-Air Force Panel on Liquid Propellant Test Methods, Silver Springs, Mdo, USA, March 1960.

The flegmatizer of the present invention suitably is an oligomer of styrene or of styrene and at least one comonomer. Preferably, the oligomer has from 2 to about 5 repeating units. More preferably, it has from 2 to about 4 repeating units. Comonomers suitably present in the preparation of the flegmatizer include, for example, α-methylstyrene, acrylonitrile, methylmethacrylate, and p-methylstyrene. Styrene oligomers and styrene-acrylonitrile oligomers are preferred. Suitably, from about 10 to about 90 percent, based on the total weight of the flegmatizer and the peroxide, of the flegmatizer is employed. Preferably, from about 25 to 75 percent of the flegmatizer is employed. Mixtures of flegmatizers can be employed.

The flegmatizers of the present invention can be readily prepared using methods well known to those skilled in the art. For example, polystyrene can be pyrolyzed/degraded at high temperature (300°–600° C.). The volatile products formed are styrene oligomers and styrene monomers. After stripping the styrene monomer from the mixture of volatile products, a syrup remains which is suitable for use as a flegmatizer.

The flegmatized organic peroxy compositions of the present invention are readily prepared by admixing the flegmatizer and the peroxide using conventional techniques.

Organic peroxy initiator compositions in accordance with the present invention are useful for initiation of polymerization of a wide variety of monomers. Among the suitable ethylenically unsaturated monomers are, for example: styrene; styrene with alkyl and halogen substituents on the ring and side chain such as o-, m- and p-methyl styrenes, alpha methyl styrene, 2,4-dimethyl styrene, 2,3-dimethyl styrene, 2,5-dimethyl styrene, alpha chlorostyrene, alpha ethyl styrene, p-ethylstyrene, m-propyl styrene, bromostyrene, dichlorostyrene, isopropenyl toluene, vinyl naphthalene, and the o-, m- and p-chlorostyrenes and bromostyrenes; esters of alpha-methylene aliphatic monocarboxylic acids, such as methyl acrylate, ethyl acrylate, n-butyl acrylate, isobutyl acrylate, dodecyl acrylate, 2chloroethyl acrylate, 2-chloropropyl acrylate, 2,2'-dichloroisopropyl acrylate, phenyl acrylate, cyclohexyl acrylate, methyl alpha-chloroacrylate, methyl methacrylate, ethyl methacrylate, methyl ethacrylate; acrylonitrile; methacrylonitrile; vinyl esters, such as vinyl acetate, vinyl chloroacetate, vinyl propionate, vinyl butyrate, vinyl laurate, vinyl stearate; vinyl ethers such as vinyl methyl ether, vinyl isobutyl ether, vinyl 2-chloroethyl ether; vinyl ketones, such as vinyl methyl ketone, vinyl hexyl ketone, methyl isopropenyl ketone; isobutylene; vinylidene halides, such as vinylidene chloride and vinylidene chlorofluoride; N-vinyl compounds such as N-vinyl pyrrole, N-vinyl carbazole, N-vinyl indole, N-vinyl succinimide; acrolein; methacrolein; acrylamide; methacrylamide; N-methylol acrylamide; and allyl compounds such as diallyl phthalate, tetrachlorodiallyl phthalate, allyl alcohol methallyl alcohol, allyl acetate, allyl methacrylate, diallyl carbonate, allyl lactate, allyl alphahydroxyisobutyrate, allyl trichlorosilane, allyl acrylate, diallyl malonate, diallyl oxalate, diallyl gluconate, diallyl methylgluconate, diallyl adipate, diallyl sebacate, diallyl citraconate, the diallyl ester of muconic acid, diallyl itaconate, diallyl chlorophthalate, diallyl dichlorosilane, the diallyl ester of endomethylene tetrahydrophthalic anhydride, triallyl tricarballylate, triallyl aconitate, triallyl citrate, traillyl cyanurate, triallyl phosphate, trimethallyl phosphate, tetraallyl silane, tetraallyl silicate, hexallyl disiloxane, and the like. Unsaturated olefins such as ethylene, propylene, butylene, hexene and exemplary monomers that can be employed with the initiators of this invention include, for example, 1,3-butadiene; isoprene; piperylene; 2,3-dimethyl-1,3-butadiene; 1,3-octadiene; 4,5-diethyl-1,3-octadiene; 3-methylstyrene; 3,5-diethylstyrene; 4-n-propylstyrene; 2,4,6-trimethylstyrene; 3-methyl-5-n-hexylstyrene; 2,3,4,5-tetramethylstyrene; 4dodecylstyrene; 4-cyclohexylstyrene; 4-phenylstyrene; 4-p-tolylstyrene; 1-vinylnaphthalene; 2-vinylnaphthalene; 4-methyl-1-vinylnaphthalene; 3-ethyl-2-vinylnaphthalene; 4,5-dimethyl-1-vinylnaphthalene; 4,5-diethyl-2vinylnaphthalene; 6-isopropyl-1-vinylnaphthalene; 2,4-diisopropyl-1-vinylnaphthalene; 4-n-propyl-5-n-butyl-2vinylnaphthalene, and the like. The styrenic monomers are preferred, with styrene being most preferred. These monomers can be employed separately, or can be copolymerized according to methods well known to those skilled in the art.

Preferred polymers which can be made according to the present invention include, for example, polystyrene, styrene/acrylonitrile, styrene/acrylonitrile/N-phenyl-maleimide, styrene/maleic anhydride, styrene/methyl methacrylate, styrene/butyl acrylate, styrene/acrylonitrile/butyl acrylate, HIPS, ABS, AES, and ABS/N-phenyl maleimide. Polymers made according to the present invention may include rubber. Polystyrene and polystyrene modified with rubber are more preferred polymers, with polystyrene being most preferred.

Polymerization of ethylenically unsaturated monomers employing the flegmatized organic peroxy compositions of the present invention may be conducted in any of the conventional polymerization systems such as bulk, mass, mass suspension, solution, suspension and emulsion polymerization. Mass polymerization is the preferred method. The flegmatized organic peroxy composition of the invention is employed in an amount sufficient to provide a conventional amount of peroxide initiator to the polymerization system. Suitably up to about 0.2 weight percent of peroxide initiator is employed based on the weight of the reaction mixture. Advantageously, from about 50 ppm to 1,000 ppm of peroxide is employed. The flegmatized organic peroxy composition suitably is added to the monomer in the conventional manner. Advantagously, this addition is performed at ambient or lower temperatures.

SPECIFIC EMBODIMENTS OF THE INVENTION

The following Examples are given to illustrate the invention and should not be construed as limiting its scope. All parts and percentages are by weight unless otherwise indicated.

EXAMPLE 1

One drop of t-butylperbenzoate is placed on a hot-plate at 400° C. resulting in immediate detonation of the peroxide and leaving a dark brown residue. The peroxide is diluted to 25% active with styrene trimer and a drop of the mixture is placed on the hot-plate at 400° C. The mixture slowly decomposes without detonation or discoloration.

EXAMPLE 2

A sample of t-butylperbenzoate is divided into two portions. One portion is flegmatized by dilution with an equal weight of a styrene-acrylonitrile (SAN) trimer which is obtained by condensing vapors which are produced by heating SAN copolymer.

A sample of styrene is divided into two portions. To one portion is added 500 ppm of t-butylperbenzoate without flegmatizer and to the other portion is added 500 ppm of SAN trimer flegmatized t-butylperbenzoate. Each of the styrene solutions is sealed in separate glass tubes (in vacuo). The sealed tubes are placed in an oil bath at 120° C. for one hour. The tubes are opened and the syrups are analyzed for molecular weight and conversion to polystyrene. The styrene conversion and the polystyrene weight average molecular weight of both samples is 25% and 250,000, respectively. The presence of the flegmatizer has no significant negative effect upon the polymerization.

What is claimed is:

1. A storage stable organic peroxide composition having reduced heat-and/or shock-sensitivity, the composition comprising an organic peroxide and from about 10 to about 90 percent, based on the total weight of the flegmatizer and the peroxide, of a flegmatizer comprising an oligomer of styrene or an oligomer of styrene and at least one comonomer, the oligomer having from 2 to about 5 repeating units.

2. The composition of claim 1 wherein the amount of flegmatizer is from about 25 to about 75 weight percent.

3. The composition of claim 1 wherein the peroxide is a perester, perketal or percarbonate.

4. The composition of claim 1 wherein the peroxide is di(t-butylperoxy)azelate or t-butyl perbenzoate.

5. The composition of claim 1 wherein the flegmatizer is an oligomer of strene-acrylonitrile or styrene.

6. The composition of claim 1 wherein the number of repeating units of the oligomer is from 2 to about 4.

7. The composition of claim 2 wherein the peroxide is a perester, perketal, or percarbonate, and the flegmatizer is an oligomer of styrene-acrylonitrile or styrene, wherein the number of repeating units is from 2 to about 4.

8. A method for reducing the heat- and/or shock-sensitivity of an organic peroxide, the method comprising admixing an organic peroxide with from about 10 to about 90 percent, based on the total weight of the flegmatizer and the peroxide, of a flegmatizer comprising an oligomer of styrene or an oligomer of styrene and at least one comonomer, the oligomer having from 2 to about 5 repeating units.

9. The method of claim 8 wherein the amount of flegmatizer is from about 25 to about 75 weight percent.

10. The method of claim 8 wherein the peroxide is t-butyl perbenzoate or di(t-butylperoxy)azelate.

11. The method of claim 8 wherein the flegmatizer is an oligomer of styrene-acrylonitrile or styrene.

12. The method of claim 8 wherein the number of repeating units in the oligomer is from 2 to about 4.

13. The method of claim 8 wherein the flegmatizer is an oligomer of styrene.

14. The composition of claim 1 wherein the flegmatizer is an oligomer of styrene.

15. The composition of claim 14 wherein the number of repeating units in the oligomer is from 2 to about 4.

16. The composition of claim 1 wherein the peroxide is benzoyl peroxide.

17. The composition of claim 1 wherein the peroxide is 2,5-dimethyl-2,5-bis(benzoylperoxy) hexane.

18. The composition of claim 1 wherein the comonomer is acrylonitrile.

19. The composition of claim 1 consisting essentially of the flegmatizer and the peroxide.

20. An organic peroxide composition having reduced heat- and/or shock sensitivity, the composition consisting essentially of an organic peroxide and from about 25 to about 75 percent, based on the total weight of the flegmatizer and the peroxide, of a flegmatizer which is an oligomer of styrene or an oligomer of styrene and at least one comonomer, the oligomer having from 2 to about 5 repeating units.

* * * * *